United States Patent [19]

Arretz

[11] Patent Number: 5,786,511
[45] Date of Patent: Jul. 28, 1998

[54] PROCESS FOR THE PREPARATION OF ORGANIC DISULPHIDES AND POLYSULPHIDES IN THE PRESENCE OF POLYSTYRENE-DIVINYL-BENZENE POSSESSING PRIMARY AMINE GROUPS

[75] Inventor: Emmanuel Arretz, Pau, France

[73] Assignee: Elf Aquitaine Production, France

[21] Appl. No.: 764,012

[22] Filed: Dec. 11, 1996

[51] Int. Cl.$^6$ .................................................. C07C 319/22
[52] U.S. Cl. .................................. 568/21; 568/25; 568/26
[58] Field of Search ..................... 568/26, 21, 25; 507/257

[56] References Cited

U.S. PATENT DOCUMENTS 3,277,180  10/1966  Biensan .
3,308,166   3/1967  Biensan .
5,068,445  11/1991  Arretz .

*Primary Examiner*—Gary Geist
*Assistant Examiner*—Jean F. Vollano
*Attorney, Agent, or Firm*—Millen, White, Zelano & Branigan, P.C.

[57] ABSTRACT

The preparation of organic disulphides and polysulphides by reaction of sulphur with a mercaptan or with a polysulphide of lower sulphur order in order to convert it into polysulphide of higher order, or alternatively by reaction of a mercaptan with an organic polysulphide of high sulphur order in order to convert it into polysulphide of lower sulphur order, in the presence of a catalyst in the form of a resin with a basic function, characterized in that the resin is based on polystyrene-divinylbenzene (PS-DVB) functionalized with primary amino groups and having the general formula (I):

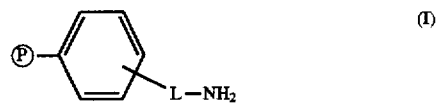

(I)

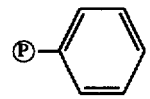

being the PS-DVB resin support, L being a linear organic radical which is as long as or longer than the methylene radical (—$CH_2$—).

15 Claims, No Drawings

PROCESS FOR THE PREPARATION OF ORGANIC DISULPHIDES AND POLYSULPHIDES IN THE PRESENCE OF POLYSTYRENE-DIVINYL-BENZENE POSSESSING PRIMARY AMINE GROUPS

CROSS REFERENCE TO RELATED APPLICATIONS

This application is related to U.S. Pat. No. 5,726,253, entitled "Process for the Preparation of Resins with a Primary Amine or Guanidine Function, and Resins Thus Obtained" by LePerchec, Abiuso, and Arretz, based on French Priority application 95/14583 filed Dec. 11, 1995, and U.S. Pat. No. 5,767,229, entitled "Process for the Preparation of Organic Disulphides and Polysulphides in the Presence of Polystyrene-Divinyl-Benzene (PS-DVB) Resins Possessing Guanidine or Amidine Groups" by Arretz and Lopez, based on French Priority application 95/14582 filed Dec. 11, 1995, all of these applications being incorporated by reference herein.

BACKGROUND OF THE INVENTION

The present invention relates to the production of organic disulphides and polysulphides R—$S_n$—R (with $n \geq 2$) by reaction of mercaptans with sulphur in the presence of basic resins which act as catalysts, according to the reaction:

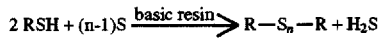

$$2\,RSH + (n-1)S \xrightarrow{\text{basic resin}} R-S_n-R + H_2S$$

In the presence of these same basic resins, organic disulphides and polysulphides of low sulphur order can be converted into polysulphides of higher sulphur order by reaction with sulphur. Similarly, in the presence of these same basic resins, organic polysulphides of high sulphur order can be converted into polysulphides of lower sulphur order by reaction with mercaptans.

Thus, patent application EP-A-337,837 teaches the preparation of organic disulphides and polysulphides in the presence of organic anion exchange resins containing tertiary amine or quaternary ammonium functional groups (active in hydroxide form). Such resins, generally in the form of grains or beads which are insoluble in liquid reaction media and are thus easy to separate out at the end of the reaction, allow polysulphides and organic disulphides to be obtained by reaction of elemental sulphur with mercaptans and also allow organic polysulphides of high sulphur order to be obtained by reaction of elemental sulphur with organic polysulphides of lower sulphur order.

S. V. Luis, M. I. Burguete and B. Altava, Reactive & Functional Polymers, 26, 1995, 75–83, indicate that the ready chloromethylation of polystyrene resins and the high reactivity of the resulting benzyl sites allows the introduction of a large number of functional groups and explains the widespread use of these polymers.

On the other hand, these authors remark that the reduced length of the methylene spacer arm reduces the mobility of the functional groups introduced and, in certain cases, makes it difficult for reactants, substrates and solvents to gain access to them. This situation may lead to a decrease in the activity of the functional groups when they are compared with their soluble counterparts. In certain cases, a marked improvement in the activity of these groups bound to the resin has been obtained when the active site is separated from the polymer skeleton by a suitable spacer arm.

S. V. Luis et al. prepare polystyrene resins having spacer arms in the form of a linear aliphatic chain containing 6 or 9 methylene groups and bearing a hydroxyl group —OH at the end of the chain.

This hydroxyl group is converted into a tosylate leaving group, the latter being replaced by substitution with a tertiary amine group.

In this synthesis, S. V. Luis et al. use functionalization of the polystyrene resin by a Friedel Crafts type reaction using the acid chloride derived from a monoalkyl ester of an alkanedioic acid.

This synthesis has the major drawback of reducing both a tosylhydrazone group and an ester group by double hydride $LiAlH_4$ in tetrahydrofuran (THF). This reduction makes this synthetic route unattractive in terms of a large-scale industrial development of resins containing these $C_6$ or $C_9$ spacer arms.

Other authors have become interested in producing spacer arms in the form of a methylene chain. Thus, M. Tomoi, N. Kori and H. Kakiuchi, Reactive Polymers, 3, 1985, 341–349, introduce a long aliphatic chain onto polystyrene resins by alkylation with ω-bromoalkenes in the presence of trifluoromethanesulphonic acid.

However, this synthesis is limited to the preparation of polymers with a spacer arm which have a low degree of crosslinking (0–4%).

Starting from a chloromethyl polystyrene resin, G. D. Darling and M. J. Fréchet, J. Org. Chem., 51, 1986, 2270–2276 have, for their part, obtained a spacer arm —$(CH_2)_2$— which separates the resin from a hydroxyl —OH at the end of the chain. This hydroxyl is converted into tosylate and then, via the Gabriel reaction using potassium phthalimide and lastly with hydrazine, into primary amine. However, this synthesis has the drawback of using n-butyllithium or lithium aluminium hydride.

SUMMARY OF THE INVENTION

An object of the present invention is to provide a process for the preparation of organic disulphides and polysulphides, according to the reactions outlined above, in the presence of functionalized and specially selected or synthesized PS-DVB resins, in order to obtain better results than those of the prior art. These better results may be, for example, a better degree of conversion of the reactants and/or faster reaction kinetics.

Upon further study of the specification and appended claims, further objects and advantages of this invention will become apparent to those skilled in the art.

The objects are achieved by the use of resins functionalized by primary amine groups —$NH_2$.

More precisely, the present invention provides a process for the preparation of organic disulphides and polysulphides by reaction of sulphur with a mercaptan or with a polysulphide of lower sulphur order in order to convert it into polysulphide of higher order, or alternatively by reaction of a mercaptan with an organic polysulphide of high sulphur order in order to convert it into polysulphide of lower sulphur order, in the presence of a catalyst in the form of a resin with a basic function, characterized in that the resin is based on polystyrene-divinylbenzene (PS-DVB) functionalized with primary amine groups and having the general formula (I):

$$\text{(I)}$$

Ⓟ—⟨phenyl⟩—L—NH₂

Ⓟ—⟨phenyl⟩ being the PS-DVB resin support, L being a linear organic radical which is as long as or longer than the methylene radical (—CH₂—).

The resins which serve as starting materials for the preparation of the resins with a primary amine function of general formula (I) may be PS-DVB copolymers or chloromethyl PS-DVB copolymers which, by appropriate chemical reactions which will be described below, are converted into resins with an —NH₂ function.

With a low content of divinylbenzene as crosslinking agent, copolymers of the gel type are obtained, whereas with higher DVB contents, macrocrosslinked resins of macroporous structure may be obtained.

The DVB contents may be from 0.5% to 60% by weight relative to the total weight of the PS-DVB copolymer.

Preferably, the starting materials and, consequently, the resins of general formula (I) are macrocrosslinked and of macroporous structure since these characteristics provide better catalytic activity in the process than resins of gel type.

These PS-DVB resins may be chloromethylated with chloromethyl ether, according to known techniques which are described in the literature, to variable chlorine (Cl) contents, generally from 1 to 20% by weight of chlorine relative to the weight of chloromethyl resin.

Preferably, the radical L represents a methylene. This is because these resins with aminomethyl groups are either commercial or are easy to synthesize.

Advantageously, the radical L has the general formula (II) below:

—CH₂—(—X—CH₂—CH₂—)$_m$—   (II)

in which X represents oxygen or sulphur and m is equal to 1 or 2.

Preferably, in the formula (II), X is oxygen and m is equal to 1, or alternatively X is sulphur and m is equal to 1.

The PS-DVB resins with a primary amine function of general formula (I) may be obtained by various techniques:

1. It is possible, for example, to start with a resin of general formula (B):

$$\text{(B)}$$

Ⓟ—⟨phenyl⟩—L—X

X being a leaving group, in particular halogen or tosylate which may be obtained from a hydroxyl group —OH, with L having the same meaning as above.

Preferably, when L represents a single methylene, X is a chlorine atom. In this case, a method, described by D. H. Rich and S. K. Gurwara, J. Am. Chem. Soc., 1975, 97-1575-1579, consists in reacting a chloromethyl PS-DVB resin with excess ammonia. Another route is based on the production of phthalimidomethyl PS-DVB resin, which is converted by hydrazinolysis into a resin with a primary amine function. The two methods for gaining access to such phthalimidomethyl resins are described in the publication by A. R. Mitchell, S. B. H. Kent, B. W. Erickson and R. B. Merrifield, Tetrahedron Letters No. 42, 1976, 3795-3798. One consists in starting with a PS-DVB resin which, on reaction with N-(chloromethyl)phthalimide, is directly converted into phthalimidomethyl resin. The other method starts with a chloromethyl PS-DVB resin which is treated with potassium phthalimide to give the corresponding phthalimidomethyl resin.

A few PS-DVB resins with a primary amine function of formula (I) in which L represents a methylene are commercial.

Thus, the company Purolite provides two macroporous resins, A-107 and A-109, whereas the company Fluka has, in its 1994-1995 catalogue, two gel resins: the resin 08564 PS crosslinked with 2% DVB and containing 1.1 mmol of —NH₂ groups per gram of resin, and the resin 08566 PS crosslinked with 1% DVB and containing 0.6 mmol of —NH₂ per gram of resin.

The method with potassium phthalimide can also be applied to the resins of formula (B) in the case where L is a linear organic radical longer than the methylene radical, in particular —(CH₂)$_n$—, with n being a number greater than 1.

2. It is also possible to start with a PS-DVB resin of formula (B) in which L represents a methylene and X has the above meaning and preferably represents a chlorine atom. It has been discovered that this chloromethyl resin can be reacted with an alkanolamine or a mercaptoalkylamine, in alkaline alkoxide form, under the Williamson reaction conditions.

If the ethanolamine is used, PS-DVB resins having a primary amine function with —CH₂—O—CH₂—CH₂—NH₂ functional groups bound to the PS-DVB resin supports are obtained.

Similarly, starting with 2-aminoethanethiol hydrochloride, —CH₂—S—CH₂—CH₂—NH₂ functional groups are obtained.

If 2-(2-aminoethoxy)ethanol is used, PS-DVB resins having a primary amine function with —CH₂(—O—CH₂—CH₂)₂—NH₂ functional groups are obtained.

Lastly, using 2-(2-aminoethyl)thioethanethiol, —CH₂—(S—CH₂—CH₂)₂—NH₂ functional groups are obtained.

This starting mercaptoalkylamine may be prepared according to Iwakura et al., J. Polym. Sci. Part A, 2, 1964, 881-883 or according to I. Voronkov, M. G. et al., Chem. Heterocycl. Compd. (Engl. Transl.) 15, 1979, 1183-1885.

The general conditions of the Williamson reaction are as follows:

The alkanolamine or the mercaptoalkylamine diluted in anhydrous tetrahydrofuran (THF) is reacted with sodium hydride suspended in anhydrous THF. After formation of the sodium alkoxide or the sodium mercaptide, the chloromethyl resin is introduced into the liquid reaction medium.

Advantageously, the mercaptans and organic disulphides and polysulphides have hydrocarbon radicals R chosen from an alkyl, cycloalkyl, aryl, aralkyl and alkylaryl group.

The present invention applies in particular to the production of dialkyl disulphides and polysulphides containing in total from 2 to 40 carbon atoms, for example dimethyl, diethyl, dipropyl, dibutyl, dipentyl, dihexyl, diheptyl, dioctyl, didecyl and didodecyl disulphide and polysulphides. It also applies to the preparation of cycloalkyl disulphides and polysulphides, for example dicyclohexyl disulphide or polysulphides, or to the preparation, for example, of diphenyl disulphide or polysulphides.

Advantageously, the hydrocarbon radical R bears one or more functional groups. These groups are, for example, halogen atoms, —OH, —OR', —SR', NR'R", CN, —CHO, —COR', —COOR', R' and R" denote $C_1$ to $C_{12}$ aliphatic radicals or cycloaliphatic, aromatic or alkylaromatic radicals.

The catalytic activity of the resins used in the present invention is detected at and above very low resin contents in the mixtures.

Advantageously, the resin is present in an amount ranging from 0.01 to 20 parts by weight per 100 parts by weight of reaction mixture, resin included.

The process according to the invention uses a reaction which may be carried out at a temperature of from $-10°$ C. to $150°$ C. The temperature is preferably from $+10°$ C. to $120°$ C.

The reactions may be performed at atmospheric pressure or at higher pressures which may reach 50 bar. In general, this pressure is 28 bar absolute. In the case of relatively non-volatile reactants of low vapour pressure, the reaction may be performed at pressures below atmospheric pressure, optionally in the presence of an inert gas, such as nitrogen.

The mercaptan/sulphur molar ratio depends on the nature of the mercaptan used and on the product to be prepared (disulphide or polysulphide). Advantageously, this ratio is from 0.3 to 10 and preferably from 0.4 to 6.

In the case where an organic polysulphide of high sulphur order is used at the start, which it is desired to convert into organic polysulphide of low sulphur order, for example into trisulphide R—$S_3$—R or disulphide R—$S_2$—R by the action of the corresponding mercaptan, advantageously, a mercaptan/polysulphide molar ratio ranging from 2 to 10 is used.

The production of organic disulphides or polysulphides in the presence of PS-DVB resins with a primary amine function may be carried out, for example, in a stirred or tubular reactor, according to a batchwise process, or by loading the reactants before reacting them, or by gradual addition of one of the reactants, or by simultaneous addition of the reactants into the reactor, or alternatively according to a continuous process with controlled addition of the reactants.

In the case where sulphur is one of the reactants (the other being a mercaptan or a polysulphide of low sulphur order), sulfur may be introduced in liquid or solid form.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patent and publications cited above and below, and of corresponding French application 95/14581, are hereby incorporated by reference.

EXPERIMENTAL SECTION

The resins are dried under a vacuum of about $4 \times 10^3$ pascal.

A) The resins used:

The company Purolite markets two macrocrosslinked PS-DVB resins with a —$CH_2$—$NH_2$ function and of macroporous structure:

Resin A-107: 4.1 meq of —$NH_2$/g of dry resin.
Resin A-109: 4.3 meq of —$NH_2$/g of dry resin.

The company Rohm and Haas markets a macrocrosslinked PS-DVB resin with a —$CH_2$—$N(CH_3)_2$ function and of macroporous structure:

Amberlyst A-21 resin: 4.4 meq of —$NH_2$/g of dry resin.

Other resins have been specially synthesized and form the examples below:

Example 1

Production of a first resin of formula (I) in which L represents —$CH_2$—.

(a) The PS-DVB resin used is a porous synthetic copolymer marketed by the company Rohm and Haas: Amberlite XAD-4.

The characteristics of this highly crosslinked macroporous resin with a high specific surface are, according to the Rohm and Haas technical sheet:

Specific surface: 750 $m^2/g$

Average pore diameter: 50 Å

Pore volume: 51%

(b) Functionalization of this resin with N-(chloromethyl) phthalimide 10 g of predried Amberlite XAD-4 resin are added to a solution composed of 0.5 ml (0.0043 mol) of tin tetrachloride in 30 ml of 1,2-dichloroethane and, with stirring and at a temperature of 60° C., a solution of 6.7 g (0.0342 mol) of N-(chloromethyl)phthalimide in 20 ml of 1,2-dichloroethane is then added. The reaction medium is kept stirring at reflux (82°–84° C.) for 5 hours. After cooling to room temperature, the resin is filtered off and washed with 1,2-dichloroethane and then with methanol.

After drying under vacuum at 60° C., 13.1 g of modified resin were obtained.

IR spectrum: ν and δ band of CO—N—CO at 1700 $cm^{-1}$ and 1710 $cm^{-1}$.

(c) Formation of the primary amine by hydrazinolysis.

12 g of the modified resin obtained are placed in 40 ml of absolute ethanol. 4.5 ml (0.092 mol) of hydrazine hydrate and 0.9 g (0.022 mol) of sodium hydroxide pellets are added to this suspension. The mixture is maintained at reflux for 48 hours. After cooling to room temperature, the resin is filtered off, washed with ethanol and then treated with aqueous 5% by weight potassium hydroxide solution. The resin is then washed with water to neutral pH, with ethanol, with acetone and with methanol. After drying under vacuum, 11 g of resin are obtained.

IR spectrum: no more characteristic bands at 1770 $cm^{-1}$ and 1710 $cm^{-1}$ for the phthalimide group —CO—N—CO—

Elemental analysis: 3.53% nitrogen corresponding to 2.52 mmol of —$NH_2$ group/g of resin.

Example 2

Production of a second resin of formula (I) in which L represents —$CH_2$—.

(a) The pre-chloromethylated PS-DVB resin has the following characteristics, determined by analysis:

Chlorine content: 19.32% by weight (Cl=5.44 meq/g of resin)

Specific surface: 22.5 $m^2/g$

Average pore diameter: 20 Å

Pore volume: 69%

(b) Functionalization of this resin with potassium phthalimide.

10 g (0.054 eq.Cl) of this chloromethyl resin are placed in a solution of 10.1 g (0.054 mol) of potassium phthalimide in 150 ml of anhydrous dimethylformamide (DMF) at a temperature of 50° C. and the suspension thus obtained is then left at this temperature for 24 hours. After cooling to room temperature, the resin is filtered off and washed with DMF, with methanol, with water, then again with methanol and lastly with acetone. After drying under vacuum, 15.4 g of resin are obtained.

(c) Formation of the primary amine by hydrazinolysis.

The above phthalimidomethyl resin (15.4 g) is placed in a solution of 6.6 ml (0.136 mol) of hydrazine hydrate in 150 ml of absolute ethanol, after addition of 1 g of sodium hydroxide pellets, and the mixture is stirred mechanically and maintained at reflux for 48 hours. The hot resin is then filtered off and washed with ethanol, then with water and, lastly, is treated with 400 ml of aqueous 10% by weight potassium hydroxide solution.

After this treatment, the resin is washed with water until neutral, then with ethanol and lastly with acetone. After drying under vacuum at 60° C., 10 g of resin are obtained.

Elemental analysis: N=5.46% by weight, i.e. a capacity of 3.92 mmol of primary amine function (—NH$_2$)/g of resin.

Example 3

Production of a third resin of formula (I) in which L represents the —CH$_2$—O—CH$_2$—CH$_2$— radical. The chloromethyl PS-DVB resin used is the same as that above in 2.a).

a) Production of the primary amine resin.

A solution of 6.1 g of 60% sodium hydride (0.1525 mol) dissolved in 150 ml of anhydrous THF (distilled over sodium) is prepared. A solution of 9.8 ml (0.1633 mol) of ethanolamine in 100 ml of anhydrous THF is added slowly to this solution under a nitrogen atmosphere. The reaction medium is kept at 20° C. with stirring for 1 hour and is then maintained at reflux for 2 hours. After cooling to 20° C., 20 g of the chloromethyl resin are introduced slowly. The reaction medium is brought to 70° C. with continued stirring and is maintained at this temperature for 48 hours. After cooling, the resin is filtered off and is then washed successively with water, with aqueous 5% by weight potassium hydroxide solution, then with water until neutral and lastly with methanol.

The resin is dried under vacuum at 60° C. and 20.1 g of the primary amine resin bearing the —CH$_2$—O—CH$_2$—CH$_2$— spacer arm are obtained.

Elemental analysis: N=4.28% by weight, i.e. a capacity of 3.05 mmol of primary amine function (—NH$_2$)/g of resin.

b) Preparation of di-n-butyl disulphide by reaction of n-butylmercaptan with sulphur in the presence of resins with an amine function.

The following tests for the preparation of di-n-butyl disulphide were carried out under identical experimental conditions, changing only the PS-DVB resins, but using for each test an amount of dry resin corresponding to the same number of basic equivalents of resins.

A comparative test was carried out with dry Amberlyst A-21 resin containing a tertiary amine function.

These tests are each carried out in a reactor consisting of a 50 ml two-necked glass conical flask fitted with a water-cooled reflux condenser and a thermometer sheath for measuring the temperature of the reaction medium. This reactor is heated by an oil bath placed on the plate of a magnetic hot-plate stirrer, and stirring is obtained by means of a Teflon-coated magnetic stirrer-bar placed in the reaction medium.

26.58 g (0.295 mol) of n-butyl mercaptan are introduced into the reactor with 4.5 g (0.147 mol) of finely ground sulphur and the resin in an amount corresponding to 0.41 to 0.44 meq of —NH$_2$ function, and the medium is then brought to 60° C. with stirring. After total disappearance of the solid sulphur (generally after 15 min.), samples are withdrawn at determined times and are analysed by gas chromatography, on a Hewlett-Packard Ultra-1 pillary column 50 m in length, to determine the di-n-butyl disulphide content thereof.

The results are featured in Table I below.

The amount by weight of di-n-butyl disulphide formed is noted as S$_2$%, as a function of the time in min.

TABLE I

| Resin reference | (A-21)* | A-107 | A-109 | Example No. 1 (—NH$_2$) | Example No. 3 (—NH$_2$) |
|---|---|---|---|---|---|
| Nature | Macroporous | Macroporous | Macroporous | Macroporous | Macroporous |
| Functionality | —CH$_2$—N(CH$_3$)$_2$ | —CH$_2$—NH$_2$ | —CH$_2$—NH$_2$ | —CH$_2$—NH$_2$ | —CH$_2$—O—CH$_2$—CH$_2$—NH$_2$ |
| (mmol/g) | 4.4 | 4.1 | 4.3 | 2.52 | 3.05 |
| Weight of resin | 0.1 g | 0.1 g | 0.1 g | 0.17 g | 0.15 g |
| Time (min.) | "S$_2$" % | "S$_2$" % | "S$_2$" % | "S$_2$" % | "S$_2$" % |
| 30 | 54.6 | 60.7 | 64.9 | 56.1 | 50.9 |
| 60 | 58.9 | 67.0 | 74.2 | 62.9 | 66.3 |
| 90 | 65.0 | 76.7 | 81.2 | 70.1 | 74.0 |
| 180 | 72.0 | 82.1 | 84.9 | 78.1 | 82.5 |
| 360 | 79.5 | 84.6 | 85.1 | 82.5 | 85.3 |

*comparative test

These results show that the macroporous resins with a primary amine function have a higher catalytic activity than that of the comparative test.

c) Preparation of di-tert-butyl polysulphides by reaction of tert-butyl mercaptan with sulphur in the presence of resins with an amine function.

These tests are performed in the same apparatus as above in b).

26.5 g (0.294 mol) of tert-butyl mercaptan are introduced, with 18 g (0.56 mol) of finely ground sulphur, followed by from 0.6 to 0.8 g of resin in an amount corresponding to 2.4 to 2.6 meq of amine.

The medium is then brought to 60° C. with stirring. The time to obtain total disappearance of the solid sulphur is noted. After reaction for 90 min. a first sample of the liquid reaction medium is withdrawn, followed by other successive withdrawals in the course of the reaction. The samples withdrawn are analysed by gas chromatography on a Hewlett-Packard Ultra-1 capillary column 50 m in length.

The results are featured in Table II below:

For each resin tested, the time after which all of the solid sulphur has disappeared by dissolution and also the tert-butyl mercaptan content (% TBM by weight) remaining in the reaction medium are noted.

chromatography on a Hewlett-Packard Ultra-1 capillary column 50 m in length.

The chromatographic monitoring makes it possible to determine the di-tert-butyl trisulphide content formed over time.

TABLE II

| Resin reference | (A-21)* | A-107 | A-109 | Example No. 3 (—NH$_2$) |
|---|---|---|---|---|
| Nature | Macroporous | Macroporous | Macroporous | Macroporous |
| Functionality | —CH$_2$—N(CH$_3$)$_2$ | —CH$_2$—NH$_2$ | —CH$_2$—NH$_2$ | —CH$_2$—O—CH$_2$—CH$_2$—NH$_2$ |
| (mmol/g) | 4.4 | 4.1 | 4.3 | 3.05 |
| Weight of resin | 0.6 g | 0.6 g | 0.6 g | 0.8 g |
| Dissolution of the sulphur | 80 min. | 90 min. | 60 min. | 80 min. |
| Time (min.) | TBM % | TBM % | TBM % | TBM % |
| 90 | 4.1 | 6.9 | 6.6 | 3.5 |
| 180 | 3.4 | 4.1 | 3.4 | 3.2 |

*comparative test

It is seen that the resin of Example No. 3 results in faster disappearance of the TBM than the resin of the comparative test.

d) Preparation of di-tert-butyl trisulphide by retrogradation by tert-butyl mercaptan of di-tert-butyl polysulphides of high sulphur order.

The di-tert-butyl polysulphide used has an average molecular mass of 250 (sulphur content of 54.4%) and a di-tert-butyl trisulphide content of 29.5%, the remainder to 100% by weight consisting of polysulphides ($S_x$ with x>3) of higher sulphur order.

The tests are performed in the same apparatus as described above in b) and c).

10 g (0.0365 mol) of di-tert-butyl polysulphide are introduced into the reactor with 19.71 g (0.219 mol) of tert-butyl mercaptan as well as the resin chosen, in an amount corresponding to 2 to 2.2 meq of amine, and the reaction medium is then brought to 60° C. with stirring. Samples are withdrawn at determined time intervals and are analysed by gas The results are featured in Table III below:

the proportion of di-tert-butyl trisulphide ($S_3$%) formed as a function of time in min. is noted.

TABLE III

| Resin reference | (A-21)* | A-107 | A-109 | Example No. 3 (—NH$_2$) |
|---|---|---|---|---|
| Nature | Macroporous | Macroporous | Macroporous | Macroporous |
| Functionality | —CH$_2$—N(CH$_3$)$_2$ | —CH$_2$—NH$_2$ | —CH$_2$—NH$_2$ | —CH$_2$—O—CH$_2$—CH$_2$—NH$_2$ |
| (mmol/g) | 4.4 | 4.1 | 4.3 | 3.05 |
| Weight of resin | 0.5 g | 0.5 g | 0.5 g | 0.7 g |
| Time (min.) | "S$_3$" % | "S$_3$" % | "S$_3$" % | "S$_3$" % |
| 30 | 50.9 | 41.6 | 44.5 | 40.9 |
| 60 | 58.5 | 51.4 | 58.6 | 50.8 |
| 120 | 65.2 | 60.5 | 78.9 | 60.1 |
| 180 | 68.8 | 69.6 | 87.8 | 69.1 |
| 240 | 70.9 | 73.1 | 90.4 | 72.1 |
| 300 | 72.8 | 78.9 | 93.8 | 75.6 |

*comparative test

It is noted here that the resin A-109 is the most active of the four and that the three resins with an —NH$_2$ function are more active than that of the comparative test.

The preceding examples can be repeated with similar success by substituting the generically or specifically described reactants and/or operating conditions of this invention for those used in the preceding examples.

Without further elaboration, it is believed that one skilled in the art can, using the preceding description, utilize the present invention to its fullest extent. The preceding preferred specific embodiments are, thereofre, to be construed as merely illustrative, and not limitative of the remainder of the disclosure in any way whatsoever.

What is claimed:

1. In a process for the preparation of organic disulphides and polysulphides by reaction of sulphur with a mercaptan or with a polysulphide of lower sulphur order so as to convert said polysulphide into a polysulphide of higher order, or by reaction of a mercaptan with an organic polysulphide of high sulphur order so as to convert the latter polysulphide into a polysulphide of lower sulphur order, in the presence of a catalyst in the form of a resin with a basic function, the improvement wherein the resin is based on polystyrene-divinylbenzene (PS-DVB) functionalized with primary amine groups and having the general formula (I):

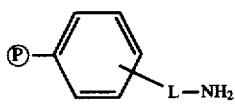
(I)

wherein:

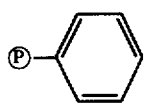

is the PS-DVB resin support, and L is a linear organic radical which is at least as long as methylene (—$CH_2$—).

2. A process according to claim 1, wherein the resin of general formula (I) is macrocrosslinked and of macroporous structure.

3. A process according to claim 1, wherein L represents a methylene (—$CH_2$—).

4. A process according to claim 1, wherein L represents a radical of formula (II)

—$CH_2$—(—X—$CH_2$—$CH_2$—)$_m$— (II)

X representing oxygen (—O—) or sulphur (—S—) and m being equal to 1 or 2.

5. A process according to claim 4, wherein X represents oxygen and m is equal to 1.

6. A process according to claim 4, wherein X represents sulphur and m is equal to 1.

7. A process according to claim 1, wherein the mercaptans and organic disulphides and polysulphides have hydrocarbon radicals R selected from a group consisting of an alkyl, cycloalkyl, aryl, aralkyl and alkylaryl group.

8. A process according to claim 7, wherein the radical R bears one or more functional groups.

9. A process according to claim 6, wherein the resin is present in an amount ranging from 0.01 to 20 parts by weight per 100 parts by weight of reaction mixture, resin included.

10. A process according to claim 1, wherein the reaction is carried out at a temperature of from −10° C. to 150° C.

11. A process according to claim 10, wherein the temperature is from +10° C. to 120° C.

12. A process according to claim 3, wherein the resin of general formula (I) is macrocrosslinked and of macroporous structure.

13. A process according to claim 4, wherein the resin of general formula (I) is macrocrosslinked and of macroporous structure.

14. A process according to claim 1, comprising reacting n-butyl mercaptan with sulfur to produce di-n-butyl disulphide.

15. A process according to claim 1, comprising reacting a di-tert-butyl polysulphide with tert-butyl mercaptan in order to produce a di-tert-butyl polysulphide of lower sulphur order.

* * * * *

UNITED STATES PATENT AND TRADEMARK OFFICE
CERTIFICATE OF CORRECTION

PATENT NO.    : 5,786,511
DATED         : July 28, 1998
INVENTOR(S)   : Arretz

It is certified that error appears in the above-identified patent and that said Letters Patent is hereby corrected as shown below:

On the title page, insert the following: --item [30], Foreign Application Priority Data
  December 11, 1995 [FR]  France.....................................95 14581 --.

Signed and Sealed this

Twenty-fifth Day of May, 1999

Attest:

Q. TODD DICKINSON

*Attesting Officer*      *Acting Commissioner of Patents and Trademarks*